United States Patent [19]

Jasper et al.

[11] Patent Number: 4,473,079

[45] Date of Patent: Sep. 25, 1984

[54] SIMPLE, SMALL, SELF-CONTAINED TESTS FOR OCCULT BLOOD

[76] Inventors: David A. Jasper, 12305 Douglas St., Omaha, Nebr. 68154; Hugh J. Phillips, 2510 N. 156th St., Omaha, Nebr. 68116

[21] Appl. No.: 416,884

[22] Filed: Sep. 13, 1982

[51] Int. Cl.³ .............................................. A61B 5/00
[52] U.S. Cl. .................... 128/638; 128/759; 422/56; 436/66
[58] Field of Search ............... 128/638, 749, 759, 760, 128/771; 604/318; 422/56, 57; 436/66

[56] References Cited

U.S. PATENT DOCUMENTS

| | | | |
|---|---|---|---|
| 3,012,976 | 12/1961 | Adams, Jr. et al. | 436/66 |
| 3,672,351 | 6/1972 | Ubersax et al. | 128/638 |
| 3,996,006 | 12/1976 | Pagano | 422/50 |
| 4,005,984 | 2/1977 | Alsop | 128/638 X |
| 4,092,120 | 5/1978 | Suovaniemi et al. | 604/318 X |

OTHER PUBLICATIONS

Winawer et al., "Current Status of Fecal Occult Blood Testing in Screening for Colorectal Cancer", CA-A Cancer Journal for Clinicians, vol. 32, No. 2, Mar./Apr. 1982.

*Primary Examiner*—Lee S. Cohen
*Assistant Examiner*—Christine A. Fukushima
*Attorney, Agent, or Firm*—Welsh & Katz, Ltd.

[57] ABSTRACT

A test for occult blood comprises an indicator that registers a chromatic change in the presence of heme and an oxygen-releasing compound, the indicator being carried on a support; a solid oxygen-releasing compound dispersed in a spreadable base and applicator to sample biological material and apply the biological material sample along with the base material-dispersed compound to the support. A chromatic change on the support indicates the presence of occult blood. An examining glove may carry the support at one location and the base material-dispersed compound at another location while a finger of the examining glove may be used as the applicator.

6 Claims, 8 Drawing Figures

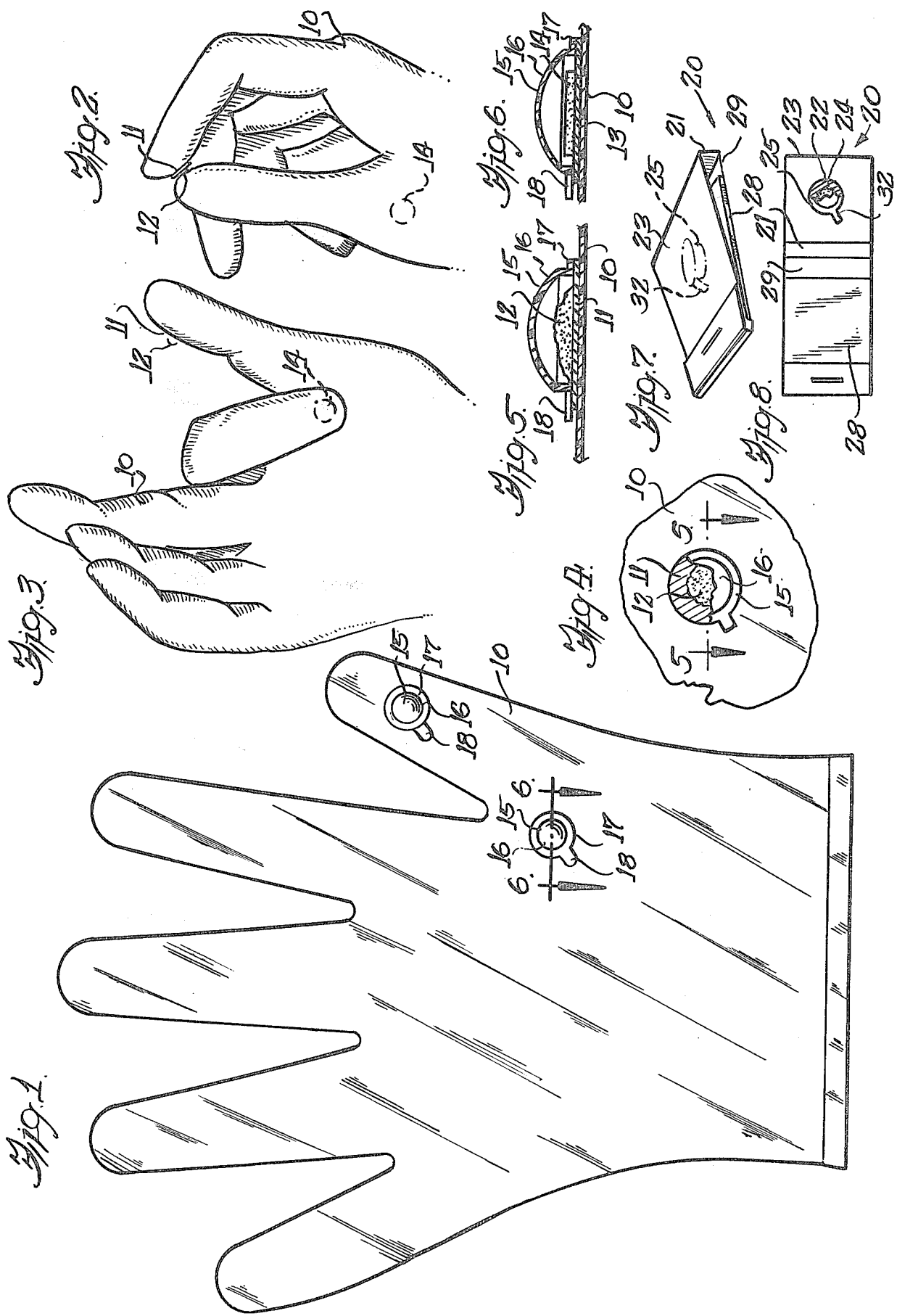

SIMPLE, SMALL, SELF-CONTAINED TESTS FOR OCCULT BLOOD

The present invention relates to tests for occult blood, and more specifically to self-contained, portable tests that are convenient to use.

BACKGROUND OF THE INVENTION

A test for occult blood is known. The method utilizes the oxygen-releasing reaction between hydrogen peroxide and hemoglobin to effect a color change in gum guaiac or benzidine derivatives.

The presence of occult blood in feces may be significant because it may indicate a digestive tract disorder, including colon cancer. Positive identification of blood in the feces usually indicates the need for determining the cause by specific testing.

Despite the opportunities and ease of testing for occult fecal blood, such testing is not routinely done. To perform a test, a doctor would need to carry a source of indicator, hydrogen peroxide and a dropper. The patient may be squeamish about the test. In some cases, slides are given to the patient with instructions to smear his own stool.

The need continues for a portable test for occult blood, all components of which are self-contained and which can be performed by a physician discreetly during routine examination in an examination room or while making hospital rounds.

SUMMARY OF THE INVENTION

A simple, portable test includes an oxidation-reduction indicator carried by a support, a solid oxygen-releasing compound dispersed in a spreadable base material, and an applicator for sampling a biological substance.

In a preferred aspect of the invention, the test materials are provided on separate regions of a physician's examining glove and the finger of the glove used as an applicator. The specimen, oxygen-releasing agent and indicator are mixed by the examining finger of the glove. Actually, the patients themselves could be given a convenient way in the form of a glove to test for occult blood.

BRIEF DESCRIPTION OF THE DRAWINGS

FIG. 1 is an elevation view of a physician's examining glove embodying various features of the present invention;

FIG. 2 is a diminutive perspective view of the glove of FIG. 1 fitted over a doctor's hand and performing one step of the test;

FIG. 3 is a perspective view, similar to that of FIG. 2, showing the next step of the test being performed;

FIG. 4 is an enlarged elevation view, partially cut away, of the test material on the thumb of the glove of FIG. 1;

FIG. 5 is an enlarged cross-sectional view taken generally along line 5—5 of FIG. 4;

FIG. 6 is an enlarged cross-sectional view taken generally along line 6—6 of FIG. 1;

FIG. 7 is a perspective view of an alternative embodiment of the present invention in the form of a portable matchbook test plate; and FIG. 8 is a plan view of the open matchbook test plate of FIG. 7.

DETAILED DESCRIPTION OF THE PREFERRED EMBODIMENTS

The portable test described herein employs a variation of the known hemoglobin; hydrogen peroxide; gum guaiac test used to detect blood in which heme catalyzes the release of oxygen from hydrogen peroxide, and oxygen changes the indicator gum guaiac from colorless to blue. In accordance with the present invention, a much more convenient, discreet test is provided by replacing the liquid hydrogen peroxide solution with a solid oxygen-releasing compound and providing means to sample a biological substance and to combine the biological sample and solid oxygen-releasing substance with an indicator on a visible surface of a support. Preferably, the solid oxygen-releasing compound is dispersed in a spreadable medium while the indicator is carried by the support. In the preferred embodiment, the solid compound dispersed in the spreadable medium and the indicator-carrying support are carried on a physician's examining glove, whereby a digit of the examining glove is used to sample the biological substance, gather spreadable medium and apply it to the support surface. Removable cover means prevent degradation of the oxygen-releasing compound and the indicator.

The indicator is carried on a support that provides a visible surface area. A convenient support is filter paper or other light colored porous material in which the indicator is impregnated. As the test, described herein, is qualitative rather than quantitative, the amount of indicator is not considered to be critical except to the extent that sufficient indicator should be present that the test may be read by the naked eye.

Generally, about 10-50 micrograms gum guaiac are applied to each $cm^2$ filter paper. The same applies to other indicators that have similar oxidation-reduction potentials, such as benzidine derivatives, e.g., benzidine, toluidine. The precise amount of indicator depends, of course, on various factors, such as the thickness of the filter paper and solubility of the indicator.

The reaction between heme and hydrogen peroxide proceeds readily in an acid environment, and an acid may be conveniently carried on the support along with the indicator. A weakly-dissociated acid which does not degrade the indicator or the filter paper is required. Organic acids, such as acetic acid, citric acid etc., are particularly suitable for application to filter paper with the indicator. Impregnation may be carried out by dissolving both the indicator and acid in a volatile solvent, such as methanol, ethanol or propanol, and drying the filter paper.

The oxygen-releasing solid compound must react with heme in a manner analogous to hydrogen peroxide. A number of solid peroxy compounds have been found suitable for this purpose. In this regard, it is found that benzoyl peroxide, sodium peroxide, magnesium peroxide and sodium perborate are particularly suitable although this list is not intended to be inclusive of the peroxy compounds which might be used in the test. Sodium perborate is a preferred compound.

The base material should provide for the dispersion of the finely divided peroxy compound and provide an environment in which the peroxy compound is stable until use. The base material also provides adhesion to a surface, and herein, a highly viscous fluid, which sticks to and is spreadable over a surface, is preferred. A suitable base material is petrolatum, which is spreadable, adhesive, non-reactive with peroxy compounds and completely safe should it inadvertently contact the patient.

A stabilizer of peroxy compounds, such as acetanilid, may also be dispersed with the compound in the base material.

A surgeon's glove 10 is illustrated in FIG. 1 and carries the test material for occult blood. An arrangement is shown which provides for discreet and almost instantaneous testing for occult blood during a rectal or other body cavity examination. A circle of aluminum foil 11 (FIG. 5) is attached with rubber cement to the inner upper surface of the thumb of the glove, and a dab of petrolatum compound 12 containing a dispersed peroxy compound is applied to the center of the aluminum foil circle. Another circle 13 (FIG. 6) of aluminum foil is cemented to the base of the thumb and a circular piece of filter paper 14, which has been impregnated with a mixture of a mild acid and indicator, is attached with an adhesive, such as Elmer's (trademark) glue, to the center of the aluminum foil.

To protect the test material from contamination prior to testing, a layer of material 15, e.g., plastic, is adhered to the glove 10 to cover the testing materials prior to testing. In the illustrated embodiment, the cover layer 15 takes the form of spherical bubbles 16 each having an outer annular flange 17 that is glued, e.g., with Elmer's (trademark) glue to the aluminum foil circles 11, 13, so that one bubble covers the petrolatum mixture 12 and the other bubble covers the filter paper 14. A pull tab 18, extending from each flange 17, facilitates removal of the covers 15 from the glove 10.

After using his glove-covered index finger to perform the rectal examination, the physician with his other hand, removes the plastic bubbles 16 from over the test materials. He then touches (FIG. 2) his index finger to the petrolatum mixture 12 at the tip of his thumb and rubs (FIG. 3) this onto the filter paper 14 at the base of his thumb. If occult blood is present, there will be an almost immediate chromatic change on the filter paper. No color change indicates the absence of occult blood.

Illustrated in FIG. 7 is a portable test 20, with the test materials provided in a matchbook 21 that the physician may carry in his pocket. A piece of aluminum foil 22 is adhered with rubber cement to the inside surface of the flap 23 of the matchbook 21; a dab 24 of petrolatum is applied generally at the center of the aluminum foil; and a plastic bubble cover 25 is glued to the aluminum foil with the bubble covering the petrolatum dab. A rectangle of filter paper 28, impregnated with a weakly-dissociated acid and the indicator, e.g., acetic acid and gum guaiac, is stapled or glued to the inside surface of the back 29 of the matchbook 21. When the physician has completed an examination that results in a digit of his surgical glove obtaining a biological sample, he opens the matchbook 21, removes the bubble 25 by lifting an extending tab 32 thereof, touches the digit to the petrolatum dab 24 and smears the sample and petrolatum on the digit across the filter paper 28. A chromatic change on the filter paper 28 is indicative of occult blood in the biological sample.

EXAMPLE 1

Ten mg of gum guaiac was dissolved in a mixture of one ml acetic acid and ten ml methyl alcohol. A 12.5 cm in diameter circular piece of Whatman (trademark) No. 42 filter paper was dipped in the solution absorbing about one ml thereof, and the filter paper was allowed to air dry. The filter paper was glued to a piece of sheet plastic.

One gm sodium perborate and thirteen mg of acetanilid were finely divided and mixed into five gm anhydrous petrolatum.

One ml of whole blood from a normal patient was diluted to a total volume of 200 ml with isotonic saline. At this dilution, the color of the blood is barely noticeable by the eye. At a first location on the filter paper, a small amount of the petrolatum composition is smeared. At a second location on the filter paper, a drop of the dilute blood is applied. At a third location on the filter paper a drop of blood is applied and a small amount of the petrolatum composition is smeared over the spot of blood application. There was no chromatic change on either the first or second location; however, after a few seconds, the third location registered a distinct blue color.

This example shows that the test is sensitive to very small amounts of blood and can detect blood at levels below that which can be detected by the naked eye.

EXAMPLE 2

Filter paper was impregnated with gum guaiac as described in Example 1 above. A petrolatum composition containing sodium perborate was also prepared as described in Example 1. On forty disposable examination gloves, circles of impregnated filter paper, the size of a penny, were glued to the bases of the thumbs. A little petrolatum composition was smeared on the thumbs of the gloves in the region of the inner surfaces of the outer joints. Forty stool specimens suspected to contain occult blood were obtained. Each stool specimen was checked by the Hemoccult (trademark) test, an accepted commercially available test for occult blood that utilizes liquid hydrogen peroxide. The stool specimens were also tested, by donning the glove, touching the tip of the index finger to the stool specimen, picking up a little of the petrolatum composition by touching the inner surface of the thumb with the index finger and pressing the tip of the index finger to the base of the thumb. Appearance of a blue color was indicative of occult blood in the stool sample and absence of a color change was indicative of no blood in the stool sample.

The results of the two methods of testing were identical, 23 stool samples registering positive for the presence of occult blood and 17 stool samples registering negative for the presence of occult blood.

The advantages of the invention can now be more fully appreciated. By substituting a solid peroxy compound dispersed in a spreadable base material for liquid hydrogen peroxide, all of the test materials are present or self-contained on an examining glove. The test can be performed within seconds requiring substantially no effort and requires no unpleasant task by the patient. The test retains the degree of accuracy of medically accepted tests using liquid hydrogen peroxide but eliminates the extra materials and technician time required to perform such tests.

While the invention has been described in terms of a preferred embodiment, modifications obvious to one with ordinary skill in the art may be made without departing from the scope of the invention. For example, the indicator could be dispersed in a spreadable base material while the oxygen-releasing compound could be carried by a support having a visible surface. The biological sample may be obtained and spread by applicators, such as cotton swabs, other than a digit of a glove.

Various features of the invention are set forth in the following claims.

What is claimed:

1. A device for testing for occult blood, comprising an examining glove,
   an indicator that registers a chromatic change in the presence of heme and an oxygen-releasing compound,
   a support on the surface of said glove carrying said indicator, said support having a surface on which a chromatic change may be noted,
   a solid oxygen-releasing compound that effects said chromatic change in the presence of heme and said indicator, and
   a spreadable base material in which said solid compound is dispersed, said base material being carried on the surface of said glove at a location remote from said indicator, whereby a biological substance may be sampled with a finger of said glove and transferred along with said base material-dispersed solid compound to said support, development of a color change on said support indicating the presence of occult blood.

2. A device according to claim 1 having removable cover means over said base material-dispersed solid compound and said indicator-carrying support.

3. A device according to claim 1 wherein said indicator is selected from a group consisting of gum guaiac, benzidine and toluidine.

4. A device according to claim 1 wherein said oxygen-releasing compound contains a peroxide group.

5. The device of claim 1 further including a removable means for covering said compound and said indicator to prevent degradation thereof.

6. The device according to claim 1 wherein said solid oxygen releasing compound is selected from the group consisting of benzoyl peroxide, sodium peroxide, magnesium peroxide and sodium perborate.

* * * * *